(12) United States Patent
Jaycox

(10) Patent No.: US 6,345,719 B1
(45) Date of Patent: Feb. 12, 2002

(54) METHODS AND APPARATUS FOR SHIPPING MEDICAL SUBSTANCES

(76) Inventor: Don Jaycox, 3923 Tamara Trail, Wildwood, MO (US) 63026

( * ) Notice: Subject to any disclaimer, the term of this patent is extended or adjusted under 35 U.S.C. 154(b) by 0 days.

(21) Appl. No.: 09/396,198

(22) Filed: Sep. 15, 1999

(51) Int. Cl.⁷ .............................................. B65D 69/00
(52) U.S. Cl. ....................... 206/570; 206/363; 206/438; 220/293; 220/915.2
(58) Field of Search ................................ 206/570, 594, 206/521, 363, 364, 366, 370, 438; 220/288, 293, 295, 297, 298, 300, 378, 915.2

(56) References Cited

U.S. PATENT DOCUMENTS

| | | | | |
|---|---|---|---|---|
| 2,078,743 A | * | 4/1937 | Traum | 220/298 |
| 2,402,360 A | * | 6/1946 | Bevins | 220/298 |
| 2,675,040 A | * | 4/1954 | Raun et al. | 220/298 |
| 3,001,668 A | * | 9/1961 | Burk et al. | 220/298 |
| 3,371,817 A | * | 3/1968 | Gasbarra et al. | 220/298 |
| 3,931,891 A | * | 1/1976 | Peppler | 220/298 |
| 4,279,355 A | * | 7/1981 | Schwartz et al. | 220/300 |
| 4,750,619 A | * | 6/1988 | Cohen et al. | 206/438 |
| 4,932,533 A | * | 6/1990 | Collier | 206/569 |
| 5,291,997 A | * | 3/1994 | He et al. | 206/370 |
| 5,560,487 A | * | 10/1996 | Starr | 206/438 |
| 5,638,976 A | * | 6/1997 | Arnold | 220/298 |
| 5,833,057 A | * | 11/1998 | Char et al. | 206/204 |
| 5,868,253 A | * | 2/1999 | Krueger et al. | 206/438 |

* cited by examiner

Primary Examiner—Shian Luong
(74) Attorney, Agent, or Firm—Armstrong Teasdale LLP

(57) ABSTRACT

A packaging system includes a packaging container, an absorbent pad, a protective wrap, an insulator, and a shipping container. The packaging container includes a vessel and a lid which attach securely together through a plurality of locking tabs and tab receptacles to form an air tight seal. The protective wrap surrounds the medical substance during shipment and limits the movement of the medical substance within the vessel. The medical substance is stored inside the vessel on the absorbent pad, the vessel is positioned within the insulator, and the insulator is placed within the shipping container.

20 Claims, 5 Drawing Sheets

METHODS AND APPARATUS FOR SHIPPING MEDICAL SUBSTANCES

BACKGROUND OF THE INVENTION

This invention relates generally to packaging systems and, more particularly, to shipping medical substances.

Biotechnology and medical research have led to the development of new medical substances which require extensive testing and verification. Often, the research facilities are located at different locations other than the testing or verification facilities. Accordingly, the medical substances must be transported between various locations. In order to protect the public and to ensure that the substances are safely transported from one location to another, intricate packaging systems are used to ensure that the substances do not escape into the environment. Current packaging systems rely on an absorbent material or fill to help prevent leakage, and thus virtually concede that some amount of spillage will occur during shipping. Accordingly, a separate liquid tight container must also be used to ensure that none of the leakage escapes to the environment. Additionally, once the absorbent material or fill is contaminated with the medical substance, an additional disposal problem is created. As a result, packaging systems in use today are typically very complicated and expensive.

BRIEF SUMMARY OF THE INVENTION

In an exemplary embodiment, a packaging system includes a packaging container which houses an absorbent pad and a protective wrap. The packaging container includes a hollow elongate vessel and a lid which secures to the vessel to form an air tight seal. The vessel includes a plurality of locking tabs which engage a plurality of tab receptacles positioned within the lid. The locking tabs are constructed of a number of different members and are tapered such that as the lid is secured, the lid and vessel are forced together. The protective wrap surrounds the medical substance during shipment and limits the movement of the medical substance within the vessel. The wrapped medical substance is stored inside the vessel on the absorbent pad which absorbs any leakage within the vessel.

The lid is secured to the vessel without the use of any external hardware and the packaging container is then placed within an insulator. The insulator includes a die-cut opening which conforms to the exterior shape of the vessel, and therefore, the vessel fits snuggly within the die-cut opening. The outer surface of the insulator is sized to fit snuggly within the shipping container. The insulator provides shock-absorbency to the vessel and prohibits the packaging container from shifting within the shipping container during shipment. Additionally, the use of the insulator provides for variations in the shape of the packaging container. As a result, the packaging system eliminates more costly and complicated known packaging systems and provides a system that is highly reliable and cost-effective.

DETAILED DESCRIPTION OF THE INVENTION

Figure 1:
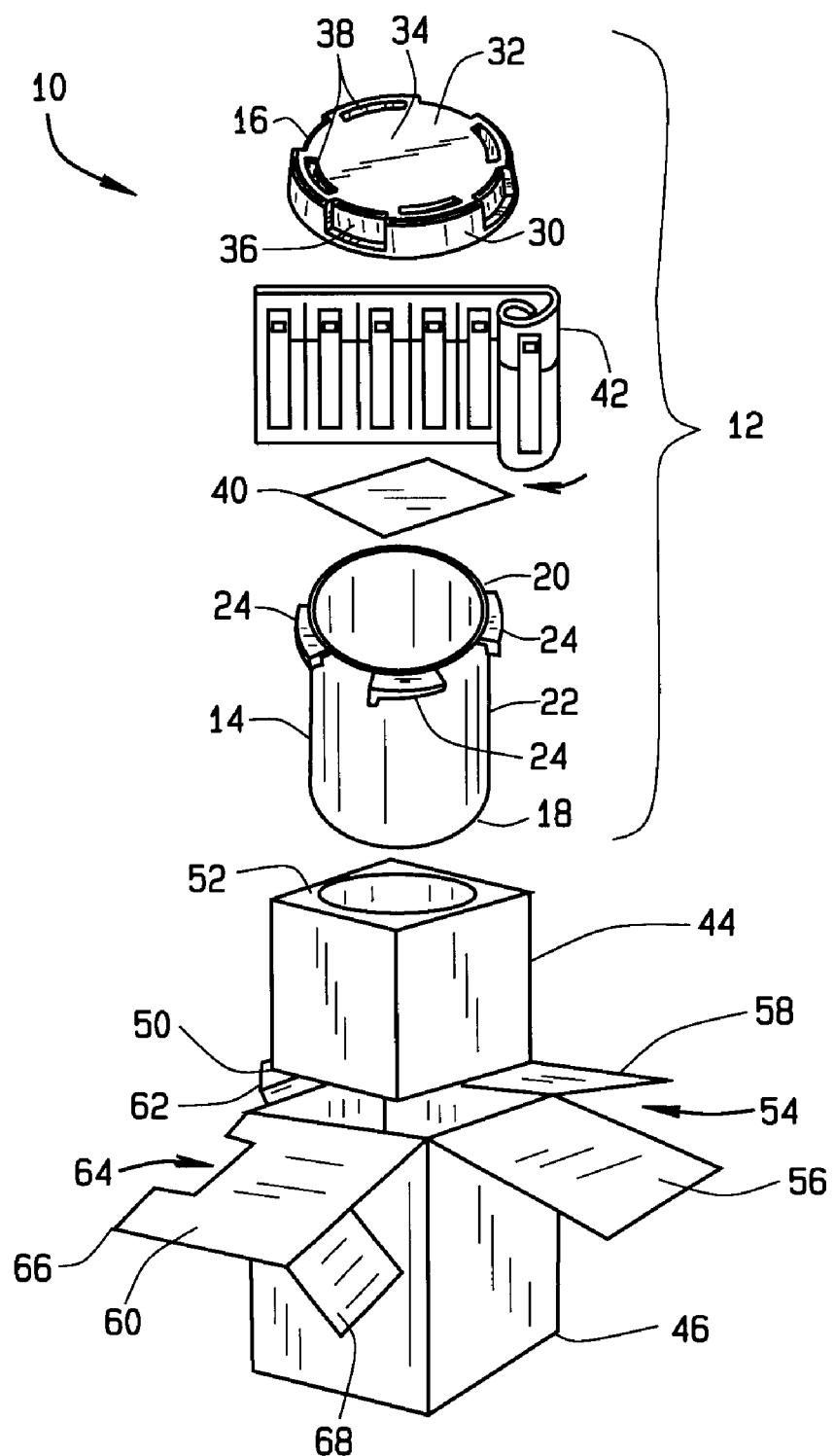
FIG. 1 is an exploded perspective of a packaging system.

FIG. 1 is an exploded perspective view of a packaging system 10 used to ship medical substances (not shown). Packaging system 10 includes a packaging container 12 for storing the medical substances during shipping. Packaging container 12 includes an elongate vessel 14 and a lid 16. Vessel 14 has a first end 18 and a second end 20. First end 18 includes a bottom wall (not shown in FIG. 1) and second end 20 is open to provide access to a hollow cylindrical body 22. Vessel 14 also includes a plurality of locking tabs 24 mounted to cylindrical body 22 in close proximity to second end 20. Locking tabs 24 extend radially outward from cylindrical body 22 and are received in a plurality of tab receptacles (not shown in FIG. 1) disposed within lid 16 when lid 16 is fully secured to vessel 14.

Lid 16 includes a cylindrical body 30 and a top wall 32. Top wall 32 has an inner surface (not shown in FIG. 1) and an outer surface 34. Cylindrical body 30 includes a plurality of notches 36 which allows a user to apply more torque to lid 16 when securing lid 16 to vessel 14. Lid 16 also includes a plurality of openings 38 which extend inward from outer surface 34. The tab receptacles are sized and spaced to receive locking tabs 24. The tab receptacles permit lid 16 to be properly oriented above vessel 14. Additionally, the locking receptacles secure lid 16 to vessel 14 when lid 16 is properly positioned with respect to vessel 14 and lid 16 is rotated one-eighth of a complete revolution.

Packing system 10 also includes a pad 40, a protective wrap 42, an insulator 44, and a shipping carton 46. Pad 40 is positioned within vessel 14 adjacent the bottom wall and beneath the medical substances being shipped. Pad 40 provides a nominal amount of shock-absorbency to the medical substances and is constructed of an absorbent material, which will contain any leakage seeping from the medical substances being shipped. In one embodiment, pad 40 is constructed from a cotton and gauze material. Protective wrap 42 is also positioned within vessel 14 adjacent pad 40 and surrounds the medical substance being shipped. Wrap 42 provides an insulating barrier between the medical substance and an inner surface (not shown) of vessel 14 cylindrical body 30. Wrap 42 is constructed of a shock-absorbent material, which limits the movement of the medical substance within vessel 14. In one embodiment, wrap 42 is constructed of a bubble wrap material.

Insulator 44 is constructed of a shock-absorbent material which is sized to fully occupy and fit snugly within a shipping carton 46. Shipping carton 46 surrounds insulator 44. In one embodiment, insulator 44 is constructed from expanded flexible polyurethane foam. Insulator 44 is die-cut such that a bottom end 50 is solid and a top end 52 is hollow. Packaging container 12 is inserted within second end 52 such that insulator 44 tightly envelops vessel 14 and provides a degree of insulation and shock-absorbency between packaging container 12 and shipping carton 46. Additionally, insulator 44 is cut to fit snuggly within shipping carton 46. Accordingly, insulator 44 prohibits packaging vessel 14 from shifting within shipping carton 46 during shipping.

Shipping carton 46 is constructed from a heavy fiberboard material and in one embodiment is constructed of 200 pound burst B-flute corrugated material with weather resistant corrugating adhesive. Shipping carton 46 includes an outer top cover 54 which includes a first inner panel 56, a second inner panel 58, a third panel 60 and an integral locking panel 62. Inner panel 56 and inner panel 58 are folded over insulator top end 52 after insulator 44 is placed within shipping carton 46. Third panel 60 includes a notch 64 along an inner side 66 which after third panel 60 is folded over insulator accepts locking panel 62. Third panel 60 also includes an integral locking flap 68 which, when used in combination with locking panel 62, securely locks outer top cover 54 in a closed position such that shipping carton 46 is in compliance with United States and International regulations regarding the shipment of medical substances.

Figure 2:
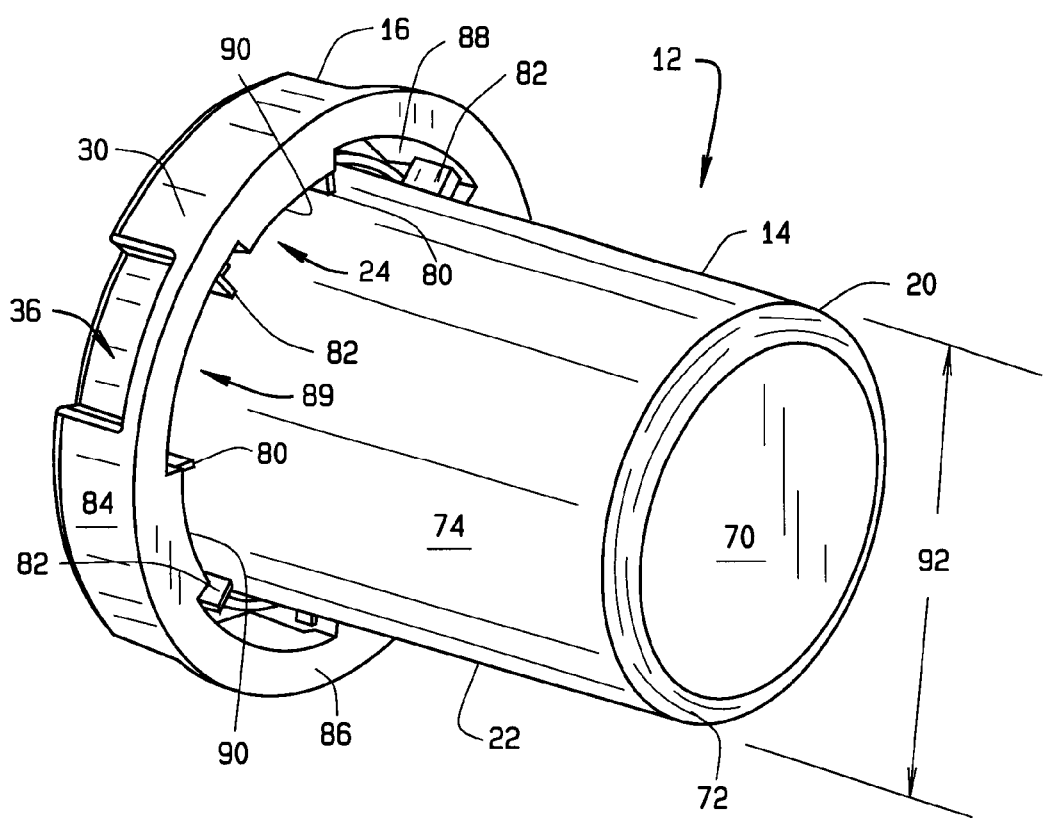
FIG. 2 is a perspective view of a packaging container used in the packaging system shown in FIG. 1.

FIG. 2 is a perspective view of packaging container 12 including vessel 14 and lid 16. A bottom wall 70 is disposed at vessel second end 20 and includes a beveled lip 72 which provides a transition surface between bottom wall 70 and cylindrical body 22. Bottom wall 70 includes an outer surface 72 and an inner surface (not shown). Cylindrical body 22 includes an outer surface 74 and an inner surface (not shown in FIG. 2). Locking tabs 24 are extend from cylindrical body 22 outer surface 74. Locking tabs 24 include a first member 80, a second member 82, a third member (not shown in FIG. 2) and a fourth member (not shown in FIG. 2). First member 80 is "L-shaped" and is mounted to and extends radially outward from cylindrical body 22 outer surface 74. Second member 82 is rectangular shaped and is mounted to and extends radially outward from cylindrical body 22 outer surface 74.

Lid 16 includes a top wall (not shown in FIG. 2) and a cylindrical body 30 which extends from the top wall. Cylindrical body 30 includes an outer surface 84, a bottom surface 86, and an inner surface 88. Outer surface 84 includes notches 36 which allows the user to apply more torque to lid 16 when securing lid 16 to vessel 14. Bottom surface 86 includes a plurality of notches 89 positioned adjacent notches 36. A plurality of tab receptacles 90 are disposed within lid 16 and are circumferentially positioned between notches 36 and 89 on inner surface 88. Cylindrical body 22 has a diameter 92. Lid 16 is sized to fit snugly over vessel 14 such that when lid 16 is fully secured, inner surface 88 is positioned substantially at diameter 92 and locking tabs 24 are received in tab receptacles 90.

Figure 3:
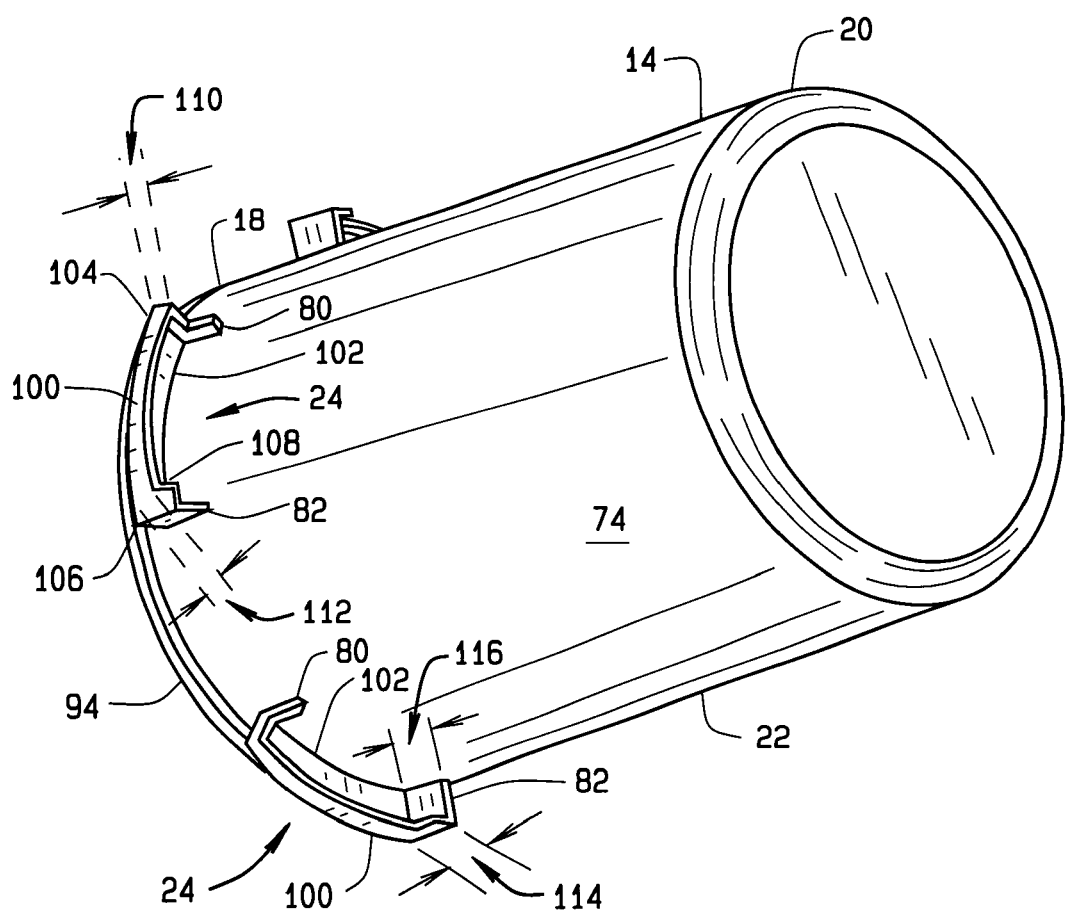
FIG. 3 is a perspective view of a vessel used in the packaging system shown in FIG. 1.

FIG. 3 is a perspective view of vessel 14 including first end 18 and second end 20. First end 18 is open and includes a seat (not shown) sized to receive an o-ring 94. O-ring 94 provides an air-tight seal between vessel 14 and a lid (not shown in FIG. 3) when the lid is fully installed upon vessel 14. First end 18 also includes a plurality of locking tabs 24. Locking tabs 24 include first m ember 80, second member 82, third member 100 and fourth member 102. First member 80 is "L-shaped" and is mounted to and extends radially outward from cylindrical body 22 outer surface 74. Second member 82 is rectangular-shaped and is mounted to and extends radially outward from cylindrical body 22 outer surface 74. When the lid is installed upon vessel 14, locking tab 24 is rotated into a tab receptacles (not shown in FIG. 3) positioned within the lid. After the lid is rotated an eighth of a complete revolution, second member 82 contacts the tab receptacles and prevents the lid from being over-tightened.

Third member 100 is mounted between first member 80 and second member 82 and has a first end 104 attached to first member 80 and a second end 106 attached to second member 82. Third member 100 is curved such that third member 100 conforms to cylindrical body 22 outer surface 74. Third member 100 is circumferentially tapered from first end 104 to an elbow 108 which is positioned in close proximity to second end 106. Third member 100 has a first thickness 110 at first end 104 and a second thickness 112 adjacent to elbow 108. Thickness 112 is greater than thickness 110. At elbow 108, third member 100 has a thickness 114 which is substantially equal to a thickness 116 of second member 82. Tapering third member 100 in such a manner permits locking tabs 24 to be tightened in the tab receptacles (not shown in FIG. 3) as the lid is rotated to a closed position. Additionally, the tapering of third member 100 draws the lid tighter against the vessel while the lid is being secured to vessel 14. Fourth member 102 is mounted to vessel 14 cylindrical body 22 and extends between first member 80 and second member 82. Fourth member 102 extends radially outward from vessel outer surface 74 and attaches to third member 100.

Figure 4:
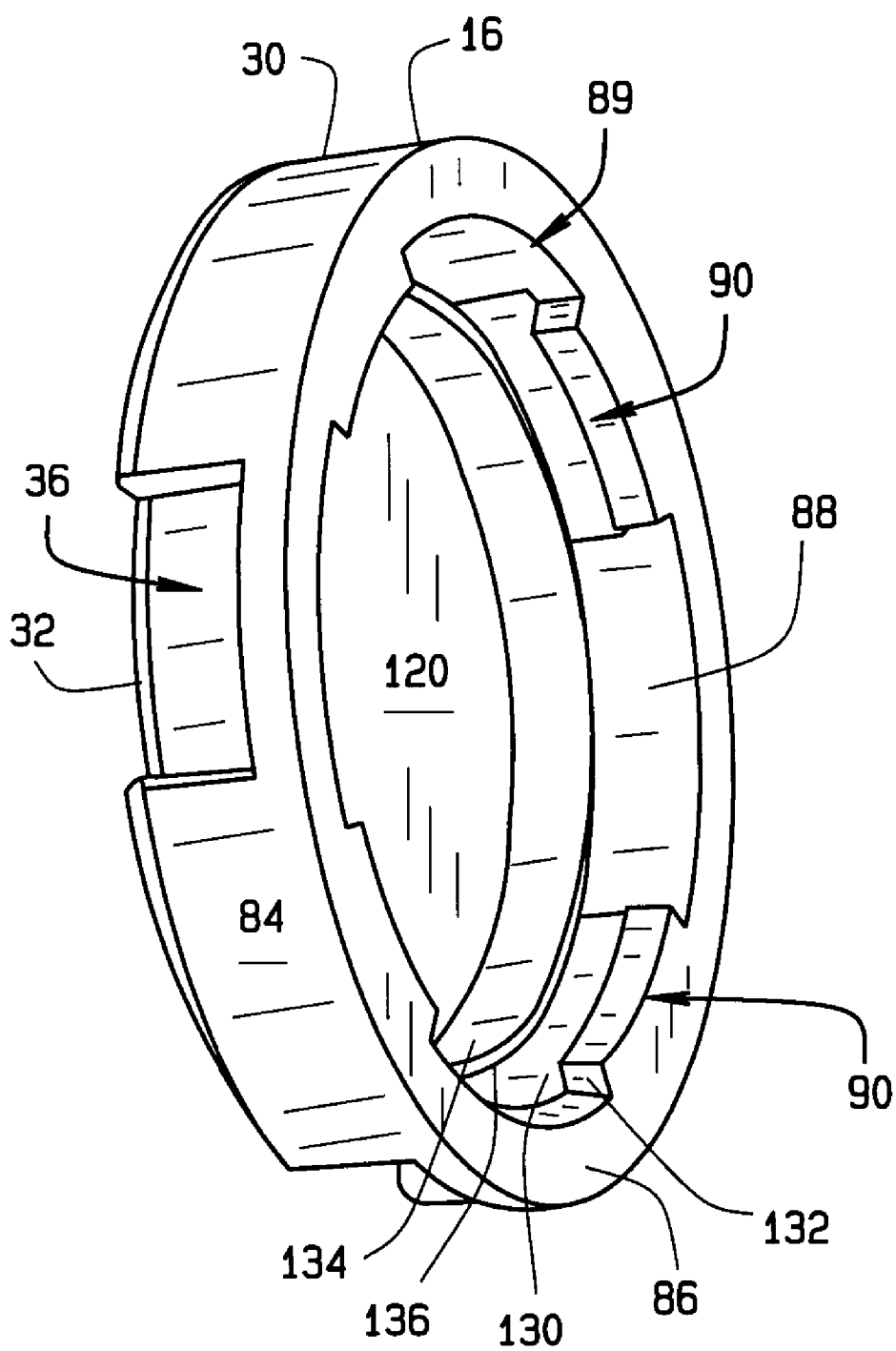
FIG. 4 is a perspective bottom view of a lid used in the packaging system shown in FIG. 1.

FIG. 4 is a perspective bottom view of lid 16 including cylindrical body 30 and top wall 32 which includes an inner surface 120. Cylindrical body inner surface 88 includes tab receptacles 90 which are spaced circumferentially between notches 89 in bottom surface 86 and notches 36 in cylindrical body 30. Tab receptacles 90 include a sleeve 130 sized to receive the locking tabs 24 (shown in FIG. 3). Sleeve 130 is formed between a shoulder 132 formed integrally with bottom surface 86 and inner surface 88 and a sealing ring 134 formed within cylindrical body inner surface 88 in close proximity to top wall inner surface 120. Sealing ring 134 provides a top surface of sleeve 130 and provides a mating surface 136 which an o-ring 94 (shown in FIG. 3) seals against when lid 16 is fully installed upon the vessel (14 shown in FIG. 3). A lip (not shown) is circumferentially mounted to lid 16 and extends from inner surface 120. The lip is configured to engage an inner surface (not shown) of the vessel when lid 16 is fully installed upon vessel and prevent any inward deflection of lid 16 when lid 16 is exposed to any pressure.

When lid 16 is being installed upon vessel 14, locking tabs 24 are initially received in notches 89. As force is applied to hold lid 16 to the vessel, lid 16 is simultaneously rotated an eighth of a revolution. The rotation forces locking tabs 24 into tab receptacles 90. As lid 16 is rotated, tab receptacles 90 force lid 16 to tighten against vessel 14 and force o-ring 94 to seal against sealing ring 134. Lid 16 is rotated closed until second member 82 (shown in FIG. 3) strikes against tab opening shoulder 132 fully securing lid 16 to vessel 14.

Figure 5:
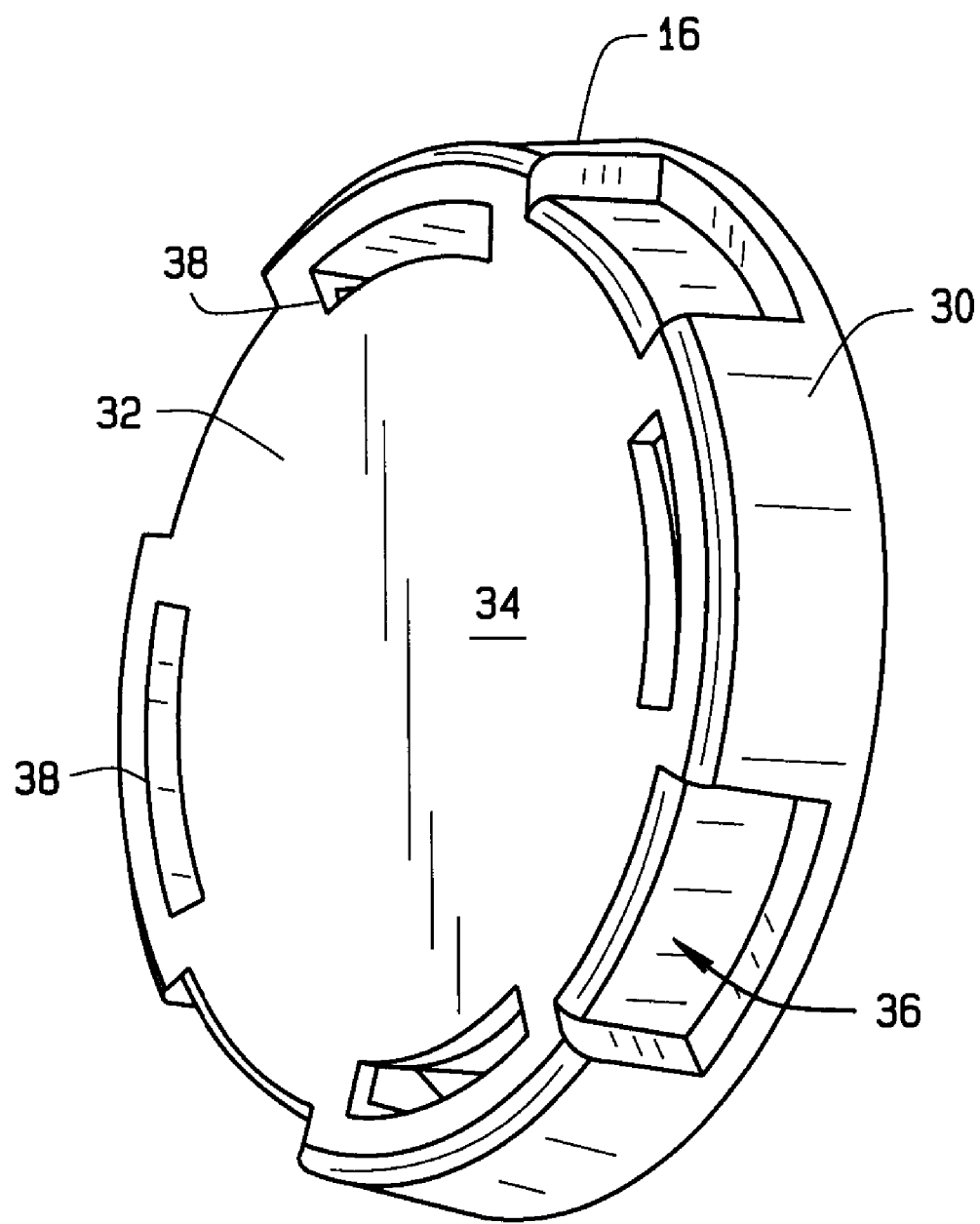
FIG. 5 is a perspective top view of the lid shown in FIG. 4.

FIG. 5 is a perspective top view of lid 16 including cylindrical body 30 and top wall 32 which includes an outer surface 34. Outer surface 34 includes receptacles 38 which extend inward from top surface 34 and are positioned above the tab receptacles (not shown in FIG. 5). Cylindrical body 30 includes notches 36 which extend from cylindrical body 30 upward to top outer surface 34. Notches 36 include a tamper-proof/resistant feature (not shown). After lid 16 is fully secured to vessel 14, a tamper resistant seal (not shown) is installed through an opening (not shown) which extends through one notch 36 into second member 82. The seal prevents lid 16 from being removed without the seal being broken.

The above described packaging system for shipping medical substances is cost-effective and highly reliable. The system includes a packaging container which includes a lid and a vessel, which in combination with each other attach to provide an air tight seal without the use of any external hardware. Furthermore, the system uses an insulator that is inexpensive and flexible enough to use with a variety of package container shapes. Accordingly, a cost effective and reliable packaging system for shipping medical substances is provided.

While the invention has been described in terms of various specific embodiments, those skilled in the art will recognize that the invention can be practiced with modification within the spirit and scope of the claims.

What is claimed is:

1. A packaging system for shipping medical substances comprising:
a packaging container for storing medical substances during shipping, said packaging container comprising an elongate vessel and a lid, said vessel comprising a bottom wall, a cylindrical body extending from said bottom wall, said cylindrical body comprising an inner surface, an outer surface, and a plurality of locking tabs mounted to said outer surface, said lid comprising a top wall, a cylindrical body extending from said top wall, a plurality of tab receptacles positioned within said lid cylindrical body, and a plurality of notches within said cylindrical body positioned between said plurality of tab receptacles, said tab receptacles configured to receive a plurality of locking tabs; and an insulator extending circumferentially around said packaging container during shipping.

2. A packaging system in accordance with claim 1 wherein said locking tabs extend radially outward from said outer surface.

3. A packaging system in accordance with claim 2 wherein said locking tabs comprise a first member mounted to said outer surface, a second member mounted to said outer surface, and a third member extending between said first member and said second member.

4. A packaging system in accordance with claim 3 wherein said locking tabs further comprise a fourth member mounted to said outer surface and extending between said first member and said second member.

5. A packaging system in accordance with claim 3 wherein said top wall comprises an inner surface, an outer surface, and a plurality of openings disposed in said outer surface.

6. A packaging system in accordance with claim 3 wherein said lid further comprises a sealing ring positioned within said lid cylindrical body and extending unitarily from said top wall.

7. A packaging system in accordance with claim 6 wherein said elongate vessel further comprises an o-ring configured to be in a sealing arrangement with said sealing ring.

8. A packaging system in accordance with claim 6 wherein said lid cylindrical body further comprises a first height and said sealing ring comprises a second height.

9. A packaging system in accordance with claim 8 wherein said first height is greater than said second height.

10. A packaging system in accordance with claim 3 wherein said third member includes a first end having a first thickness, and a second end having a second thickness greater than said first thickness.

11. A packaging system in accordance with claim 3 wherein said first member is L-shaped, said second member is rectangular-shaped, and said third member is L-shaped and curved such that said third member is substantially parallel to said outer surface of said cylindrical body.

12. A packaging system in accordance with claim 3 further comprising a shipping carton for surrounding said insulator and said packaging container during shipping.

13. A packaging system in accordance with claim 1 wherein said plurality of notches positioned adjacent said top wall.

14. A packaging system in accordance with claim 1 wherein said insulator configured to conform to said cylindrical body.

15. A packaging system in accordance with claim 1 wherein said plurality of locking tabs comprises four locking tabs spaced evenly around said outer surface of said cylindrical body.

16. A method for shipping medical substances using a packaging system including an elongate vessel and a lid, the vessel including a bottom wall, a cylindrical body extending from the bottom wall and including an inner and an outer surface, and a plurality of locking tabs mounted to the outer surface, the lid including a top wall, a cylindrical body extending from the top wall, and a plurality of receptacles positioned within the lid cylindrical body, said method comprising the steps of:
securing the medical substance within the elongate vessel; and
receiving the locking tabs in the receptacles utilizing a plurality of notches on an outer surface of the lid, the notches positioned between the receptacles.

17. A method in accordance with claim 16 wherein said locking tabs extend radially outward from the outer surface, the locking tabs including a first member mounted to the outer surface, a second member mounted to the outer surface, and a third member attached between the first member and the second member, said step of securing the medical substance within the elongate vessel further comprises the step of attaching the lid to the vessel.

18. A method in accordance with claim 17 wherein said step of attaching the lid to the vessel further comprises the step of rotating the lid upon the vessel such that the locking tabs positioned on the vessel are received within the receptacles positioned on the lid.

19. A method in accordance with claim 18 wherein said step of attaching the lid to the vessel further comprises the step of attaching the lid to the vessel wherein the lid further includes a sealing ring positioned within the lid cylindrical body and extending unitarily from the top wall.

20. A method in accordance with claim 19 wherein the elongate vessel further includes an o-ring configured to be in a sealing arrangement with the sealing ring, said step of securing the medical substance within the elongate vessel further comprises the step of attaching the lid to the vessel such that the o-ring is in a sealing arrangement with the sealing ring.

* * * * *